Figure 1A:
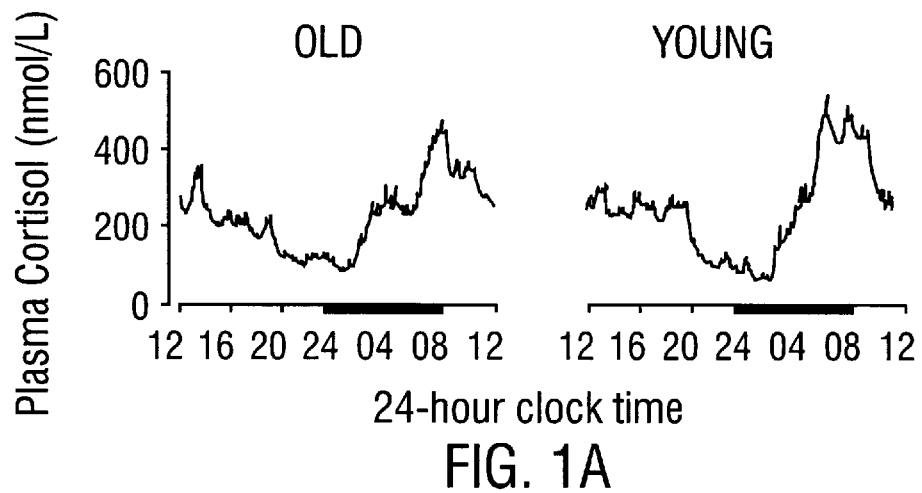

United States Patent [19]
Van Cauter et al.

[11] Patent Number: 5,840,331
[45] Date of Patent: Nov. 24, 1998

[54] USE OF γ-HYDROXYBUTYRATE FOR THE STIMULATION OF SLEEP-RELATED SECRETION GROWTH HORMONE AND PROLACTIN

[75] Inventors: Eve Van Cauter, Chicago, Ill.; Martin B. Scharf, Cincinnati, Ohio

[73] Assignee: Arch Development Corporation, Chicago, Ill.

[21] Appl. No.: 485,059

[22] Filed: Jun. 7, 1995

[51] Int. Cl.⁶ ..................................... A61K 9/20
[52] U.S. Cl. .................... 424/464; 424/451; 514/557; 514/923; 514/962; 514/2
[58] Field of Search ................... 424/401, 451, 424/464; 514/962, 557, 923, 2

[56] References Cited

U.S. PATENT DOCUMENTS

| | | | |
|---|---|---|---|
| 4,599,355 | 7/1986 | Kluger et al. | 514/533 |
| 4,738,985 | 4/1988 | Kluger et al. | 514/533 |
| 5,167,228 | 12/1992 | Czeisler et al. | 128/395 |
| 5,206,235 | 4/1993 | Fisher et al. | 514/213 |

OTHER PUBLICATIONS

Bluet–Pajot et al., "Growth Hormone Response to Hypoglycemia under Gamma–Hydroxybutyrate Narco–Analgesia in the Rat," *Neuroendocrinology*, 26:141–149, 1978.

Born et al., "The Significance of Sleep Onset and Slow Wave Sleep for Nocturnal Release of Growth Hormone (GH) and Cortisol," *Psychoneuroendocrinology*, 13(3):233–243, 1988.

Chin et al., "Acute Poisoning From γ–Hydroxybutyrate in California," *West J Med*, 156:380–384, Apr. 1992.

Degerblad et al.. "Physical and psychological capabilities during substitution therapy with recombinant growth hormone in adults with growth hormone deficiency," *Acta Endocrinololgica (Copenh)*, 123:185–193, 1990.

Dyer, "γ–Hydroxybutyrate: A Health–Food Product Producing Coma and Seizurelike Activity," *American Journal of Emergency Medicine*, 9(4):321–324, Jul. 1991.

Ehlers et al., "Effects of Corticotropin–Releasing Factor and Growth Hormone–Releasing Factor on Sleep and Activity in Rats," *Neuroendocrinology*, 42:467–474, 1986.

Finkelstein et. al., "Age–Related Change in the Twenty––Four–Hour Spontaneous Secretion of Growth Hormone," *JCE & M*, 35(5):665–670, 1972.

Garry et al., "Diurnal administration of human growth hormone–releasing factor does not modify sleep and sleep–related growth hormone secretion in normal young men," *Acta Endocrinologica*, 110:158–163, 1985.

Golstein et al., "Effects of Jet Lag on Hormonal Patterns.IV.Time Shifts Increase Growth Hormone Release," *Journal of Clinical Endocrinology and Metabolism*, 56(3):433–440, 1983.

K. Y. Ho et al., Effects of Sex and Age on the 24–Hour Profile of Growth Hormone Secretion in Man: Importance of Endogenous Estradiol Concentrations, *Journal of Clinical Endocrinology and Metabolism*, 64(1):51–58, 1987.

Iranmanesh et al., "Nature of altered Growth Hormone Secretion in Hyperthyroidism," *Journal of Clinical Endocrinology and Metabolism*, 72(1):108–115.

Iranmanesh et al., "Age and Relative Adiposity Are Specific Negative Determinants of the Frequency and Amplitude of Growth Hormone (GH) Secretory Bursts and the Half–Life of Endogenous GH in Healthy Men," *Journal of Clinical Endocrinology and Metabolism*, 73(5):1081–1088.

Isikoff, "FDA Calls Bodybuilding Drug 'Dangerous'," *The Washington Post*, Mar. 1991.

(List continued on next page.)

Primary Examiner—Raj Bawa
Attorney, Agent, or Firm—Arnold, White & Durkee

[57] ABSTRACT

Methods for reestablishing normal nocturnal growth hormone and prolactin secretion in adults with low slow-wave (deep) sleep are provided. In particular, methods are disclosed where γ-hydroxybutyrate is orally administered to subjects just prior to retiring.

21 Claims, 12 Drawing Sheets

OTHER PUBLICATIONS

Jarrett et al., "A Reexamination of the Relationship Between Growth Hormone Secretion and Slow Wave Sleep Using Delta Wave Analysis," *Biol Psychiatry*, 27:497–509, 1990.

Kerkhofs et al., "Sleep–promoting effects of growth hormone–releasing hormone in normal men," *American Physiological Society* E594–E598.

Lang et al., "Effects of Sex and Age on Growth Hormone Response to Growth Hormone–Releasing Hormone in Healthy Individuals," *Journal of Clinical Endocrinology and Metabolism*, 65(3):535–540.

Mamelak et al., "Treatment of Narcolepsy with γ–Hydroxybutyrate. A Review of Clinical and Sleep Laboratory Findings," *Sleep*, 9(1):285–289, 1986.

McCracken et al., "Dose–Dependent Effects of Scopolamine on Nocturnal Growth Hormone Secretion in Normal Adult Men: Relation to δ–Sleep Changes," *Journal of Clinical Endocrinology and Metabolism*, 72(1):90–95.

McGauley, "Quality of Life Assessment Before and After Growth Hormone Treatment in Adults with Growth Hormone Deficiency," *Acta Paediatr Scand*, 356:70–72, 1989.

Obal, Jr., et al., "Growth hormone–releasing factor enhances sleep in rats and rabbits," *American Journal Physiology*, 255:R310–R316, 1988.

Obál, Jr., et al., "Growth Hormone Releasing Hormone (GHRH In Sleep Regulation," *Sleep Res.*, 20A–192, 1991a.

Obál, Jr. et al., "Inhibition of growth hormone–releasing factor suppresses both sleep and growth hormone secretion in the rat," *Brain Research*, 557:149–154, 1991.

Oyama et al., Effects of Gamma–Hydroxybutyrate on Plasma Hydrocortisone Concentration in Man, *Anesthesia and Analgesia . . . Current Researches*, 47(4):350–354, Jul.–Aug., 1968.

Oyama et al., "Effects of gamma–hydroxybutyrate on plasma levels of Acth and cortisol in man," *Agressologie*, 10(5):411–414, 1969.

Oyama and Takiguchi, "Effects of gamma–hydroxybutyrate and surgery on plasma human growth hormone and insulin levels," *Agressologie*, 11(3):289–298, 1970.

Prinz et al., "Plasma Growth Hormone During Sleep in Young and Aged Men[1,2,3]," *Journal of Gerontology*, 38(5):519–524, 1983.

Sassin et al., "Human Growth Hormone Release: Relation to Sow–Wave Sleep and Sleep–Waking Cycles," *Science*, 165:513–515, Aug. 1969.

Scharf et al., "The Effects and Effectiveness of γ–Hydroxybutyrate in patients with Narcolepsy," *The Journal of Clinical Psychiatry*, 46(6):222–225, Jun. 1985.

Shibasaki et al., "Age–Related Changes in Plasma Growth Hormone Response to Growth Hormone–Releasing Factor In Man," *Journal of Clinical Endocrinology and Metabolism*, 58(1):212–214, 1984.

Steiger, et al. "Sleep–electroencephalography and the secretion of cortisol and growth hormone in normal controls," *Acta Endocrinologica (Copenh)*, 116:36–242, 1987.

Steiger et al., Changes of Sleep–EEG and Nocturnal Hormonal Secretion Under Pulsatile Application of GHRH or Somatostatin, *Sleep Res.*, 20A:195, 1991.

Takahara et al., "Stimulatory Effects of Gamma–Hydroxybutyric Acid on Growth Hormone and Prolactin Release in Humans," *J Clin Endocrinol Metab*, 44:1014–1017, 1977.

Van Cauter et al., "Circadian and Sleep–Related Endocrine Rhythms in Schizophrenia," *Arch Gen Psychiatry*, 48:348–356, Apr. 1991.

Van Cauter et al., "Sleep, Awakenings, and Insulin–Like Growth Factor–I Modulate the Growth Hormone (GH) Secretory Response to GH–Releasing Hormone," *Journal of Clinical Endocrinology and Metabolism*, 74(6):1451–1459, 1992.

Van Cauter et al., "A Quantitative Estimation of Growth Hormone Secretion in Normal Man: Reproducibility and Relation to Sleep and Time of Day," *Journal of Clinical Endocrinology and Metabolism*, 74(6):1441–1450, 1992.

Van Coevorden et al., "Neuroendocrine rhythms and sleep in aging men," *Am. Physiol. Soc.*, 91:E651–E661, 1991.

Vermeulen, "Nyctohemeral Growth Hormone Profiles in Young and Aged Men: Correlation with Somatomedin–C Levels," *Journal of Clinical Endocrinology and Metabolism*, 64(5):884–888, 1987.

Vickers, "Gammahydroxybutyric Acid," *International Anesthesiology Clinics*, 7:75–89, 1967.

Weiss, "A Shot At Youth," *Health*, 39–47, Nov./Dec. 1993.

Wolinsky, "Humans Vital For Research To Succeed," *Chicago Sun–Times*, Aug. 1993.

Gerra et al., "Flumazenil effects on growth hormone response to gamma–hydroxybutyric acid," *International Clinical Psychopharmacology*, 9:211–215 (1994).

Burov and Viglinskaya, "Effects of Psychotropic Drugs on Sleep Disturbances During Alcohol Withdrawal in Rats," *Bulleten Eksperimetalnoi Biologii I Meditsiny*, 91(6):689–691, 1981.

Mamelak et al., "The Effects of γ–Hydroxybutyrate on Sleep," *Biological Psychiatry*, 12(2):273–288, 1977.

Scharf et al., "Current Pharmacologic Management of Narcolepsy," *American Family Physician*, 38(1):143–148, 1988.

Takahara et al., "Inhibitory Effects of Substance P on the Gamma–Amino–Butyric Acid and Gamma–Hydroxybutyric Acid–Induced Growth Hormone and Prolactin Release in Male Rates," *Life Sciences*, 29(12):1229–1233, 1981.

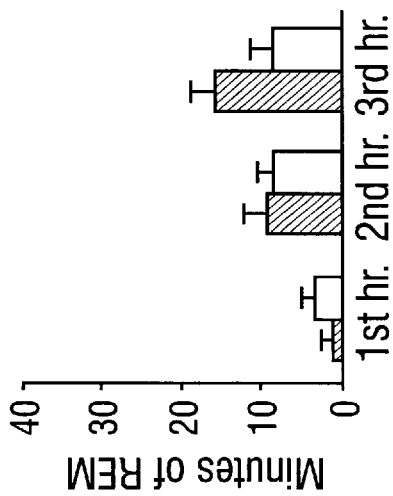
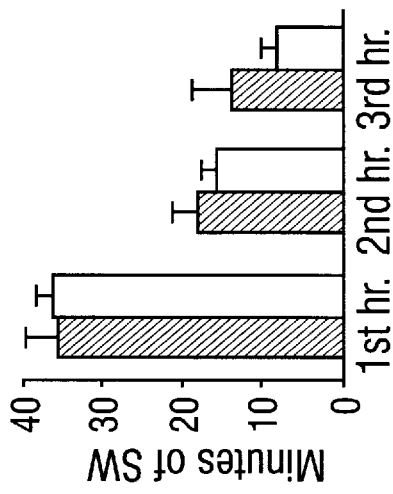
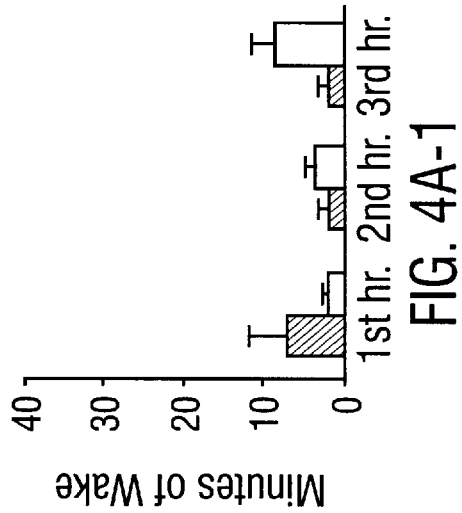
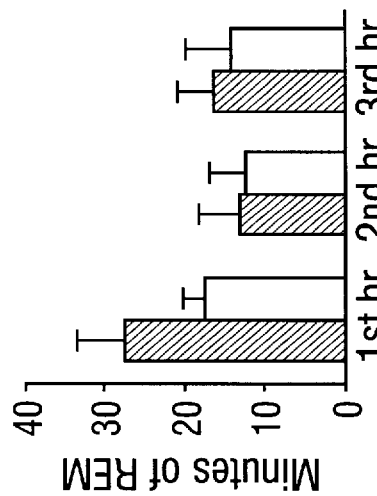
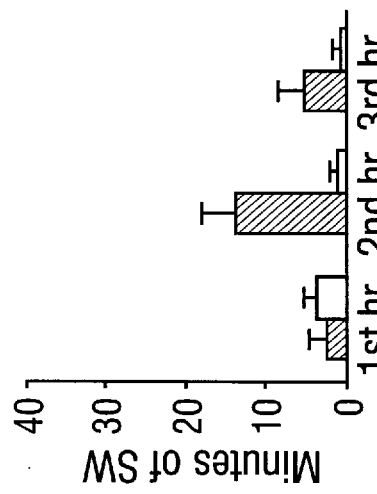
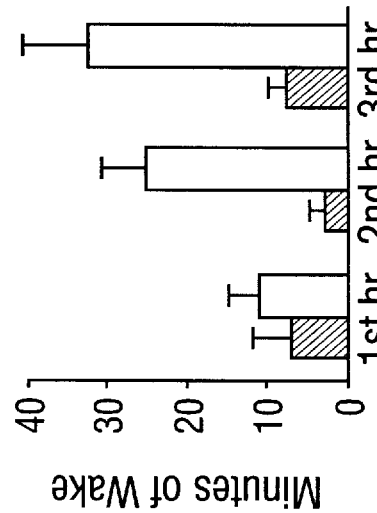

USE OF γ-HYDROXYBUTYRATE FOR THE STIMULATION OF SLEEP-RELATED SECRETION GROWTH HORMONE AND PROLACTIN

The government may own certain rights in the present invention pursuant to a grant from the National Institutes of Health DK41814.

I. FIELD OF THE INVENTION

The present invention relates to the fields of sleep therapy, gerontology and hormonal disorders. In particular, the invention addresses sleep deficiencies that are associated with depressed levels of growth hormone and the effects these changes have on aging persons.

II. RELATED ART

In young adults, sleep is associated with marked hormonal changes, including increased release of growth hormone (GH) and elevated levels of peripheral melatonin concentrations. A pulse of GH occurs shortly after sleep onset in association with the first episode of slow-wave sleep (SWS) and often represents 50–100% of the total daily GH output. There is good evidence to indicate that the nocturnal release of GH contributes to the maintenance and quality of sleep.

In older adults, sleep is disturbed with more awakenings, less SWS and less rapid eye movement (REM) sleep. The most dramatic change is the decrease in SWS, which often represents less than 5% of the sleep period time or, sometimes, disappears entirely in aged individuals. Simultaneously, growth hormone secretion also is markedly decreased, both during sleep and wakefulness. Since sleep-related GH secretion represents the major part of total GH secretion, the reduction or absence of SWS in the elderly plays a major role in contributing to the overall decline in GH secretion. The absence of activation of the GHRH-GH axis in early sleep also may be involved in the fragmentation, shallowness and reduced duration of mid and late sleep.

The implications of reduced GH secretion may be inferred from the findings in untreated GH-deficient adults, i.e., subjects who have no GH secretion due to either a congenital defect or pituitary disease. Pathologic states found in such individuals include increased cardiovascular mortality, reduced exercise capacity, reduced muscle strength, subnormal kidney function, defective sweat and temperature regulation, reduced energy expenditure and basal metabolic rate, abnormal thyroid hormone metabolism, increased fat mass, decreased lean body mass, upper body obesity and reduced bone mineral content. All of these abnormal conditions can be partially corrected by expensive GH replacement therapy with synthetic human GH. Most of the aforementioned abnormalities also are present in elderly adults who, incidentally, also have very low levels of GH secretion. Clinical trials with elderly subjects have shown the beneficial effects of GH replacement therapy, similar to that observed in GH-deficient subjects.

Unfortunately, treatment with GH injections results in an unphysiological profile of circulating GH levels, i.e., continuously elevated levels as compared to the intermittent pulses that characterize normal GH secretion, and this may be responsible for the development of the undesirable side effects which have been observed in long term treatments, including joint problems (carpal tunnel syndrome), water retention and impaired glucose tolerance. Thus, there remains a need for alternatives to GH replacement that provide an effective therapeutic means for increasing levels of GH secretion in subjects exhibiting reduced GH levels.

III. SUMMARY OF THE INVENTION

Therefore, it is an object of the present invention to provide methods of increasing slow-wave sleep in persons exhibiting low levels of SWS. It also is an object of the present invention to increase the levels of GH secretion and, in addition, alleviating other conditions associated with low GH levels.

In fulfilling these objects, there is provided a method for stimulating the release of growth hormone or prolactin in a subject comprising the steps of (a) identifying a subject having age-related suppression of growth hormone or prolactin release; and (b) orally administering to said subject, within one hour prior to retiring, an amount of γ-hydroxybutyrate effective to increase the release of growth hormone or prolactin.

In one embodiment, the subject is at least forty years old and, in another embodiment, the subject is at least sixty years old. In still another embodiment, the subject is experiencing difficulty sleeping. And in still another embodiment, the administration occurs one-half hour prior to retiring.

There also is provided as set out above, further comprising coadministering at least one growth hormone secretagogue. In one embodiment of this method, the growth hormone secretagogue is growth hormone releasing peptide or a functional analog thereof.

In another embodiment, the effective amount of gamma-hydroxybutyrate is 2.0–5.0 grams. In yet other embodiments, the effective amount of gamma-hydroxybutyrate is 2.5 grams, 3.0 grams or 3.5 grams.

There further is provided a method for stimulating the release of growth hormone or prolactin in a subject comprising the steps of (a) identifying a subject in a catabolic state; and (b) orally administering to said subject an amount of γ-hydroxybutyrate effective to increase the release of growth hormone or prolactin. In other embodiments, wherein said catabolic state is the result of severe trauma, such as burns, surgery or chronic illness.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

IV. BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1A. Mean 24 hour profiles of plasma cortisol in old and young subjects. Distribution of sleep stages is expressed in minutes in each 15 min. interval between blood samplings spent in SW or REM stage. Vertical lines represent SE. Black bars correspond to mean sleep time.

Figure 1B:
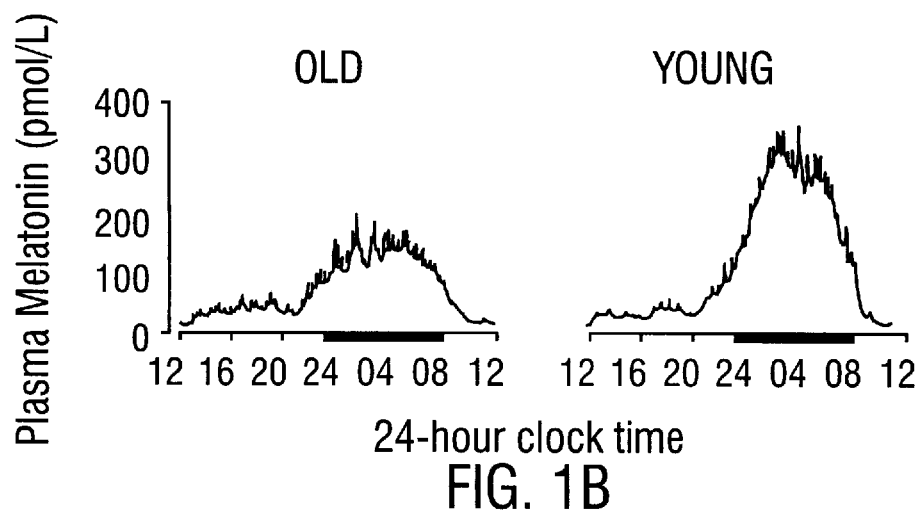

FIG. 1B. Same as FIG. 1A except data is plasma melatonin.

Figure 1C:
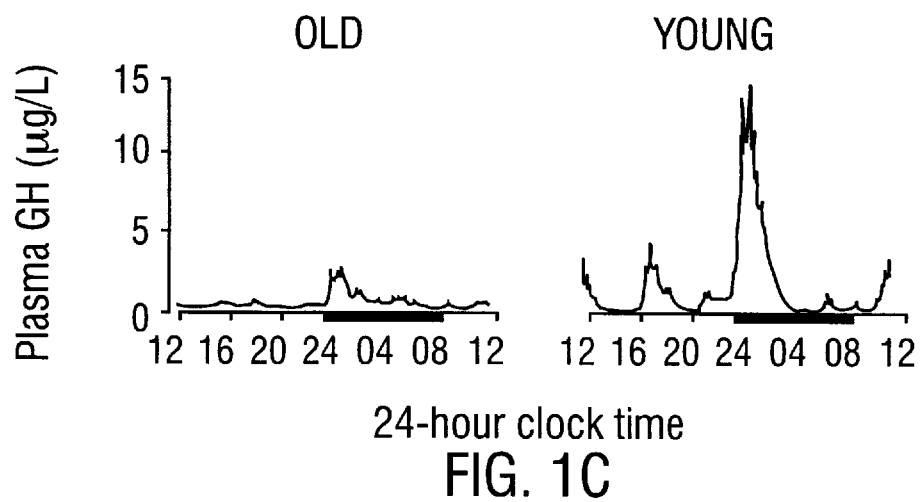

FIG. 1C. Same as FIG. 1A except data is plasma GH.

Figure 1D:
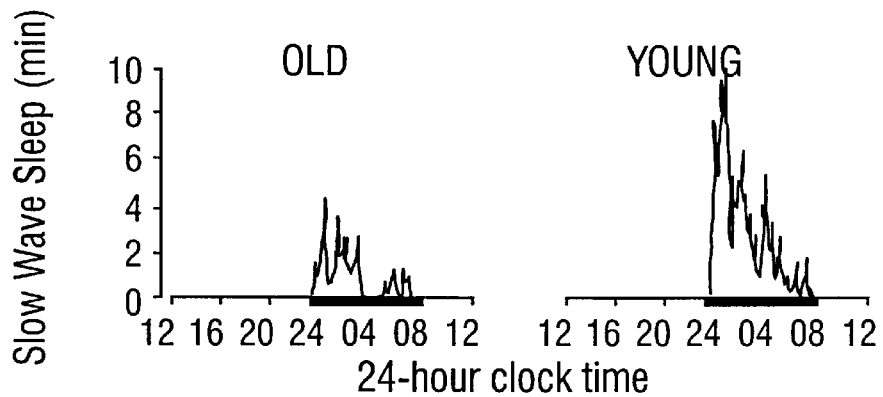

FIG. 1D. Same as FIG. 1A except data is SWS.

Figure 1E:
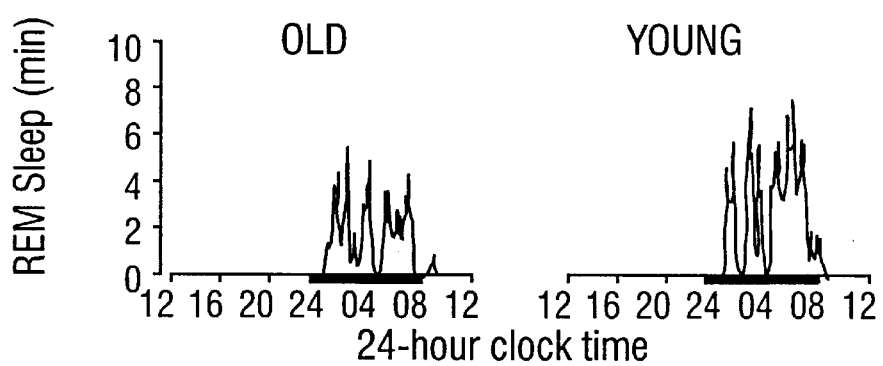

FIG. 1E. Same as FIG. 1A except data is REM sleep.

Figure 2:
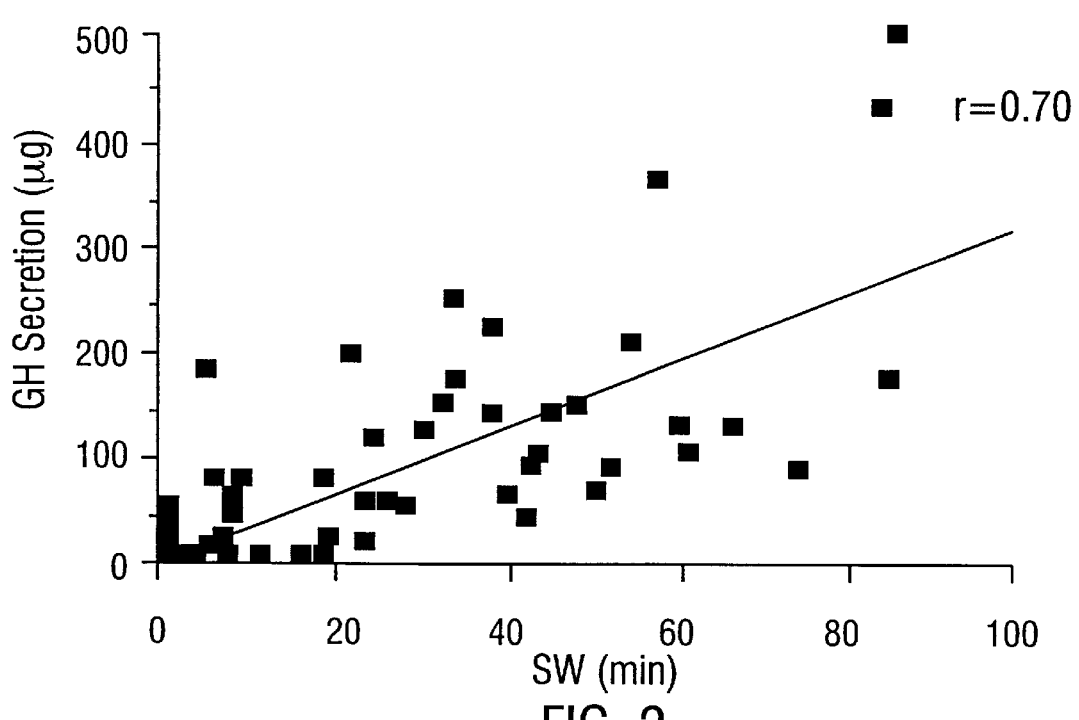

FIG. 2. Correlation between amount of GH secreted in nocturnal pulses and amount of SW sleep occurring during the pulse.

Figure 3:
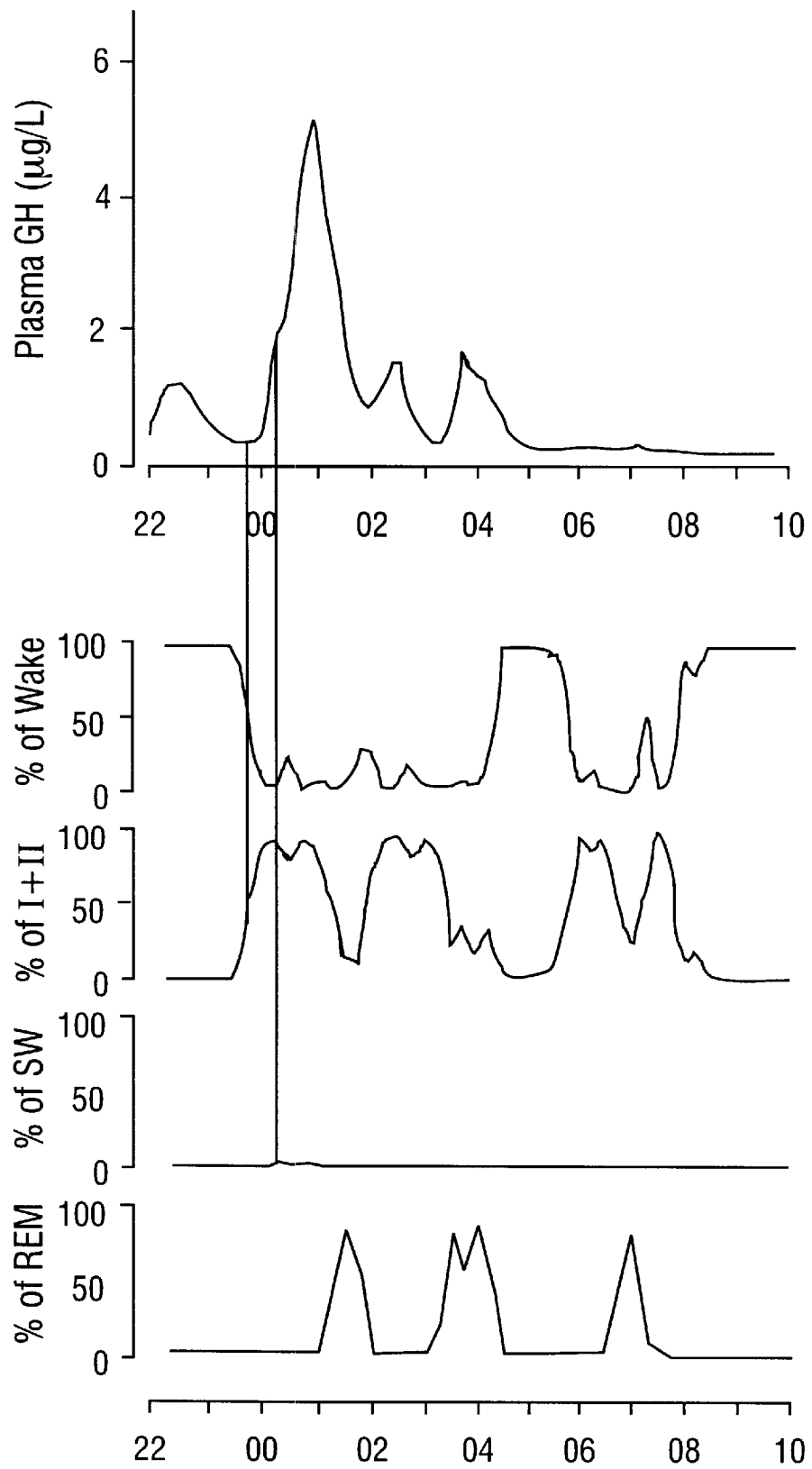
Figures 1, 5A:
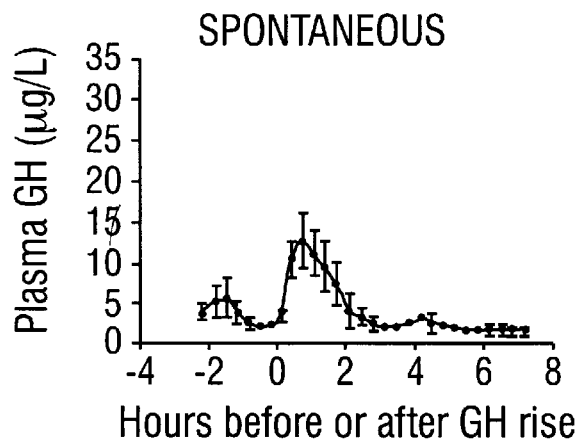
Figures 2, 5A:
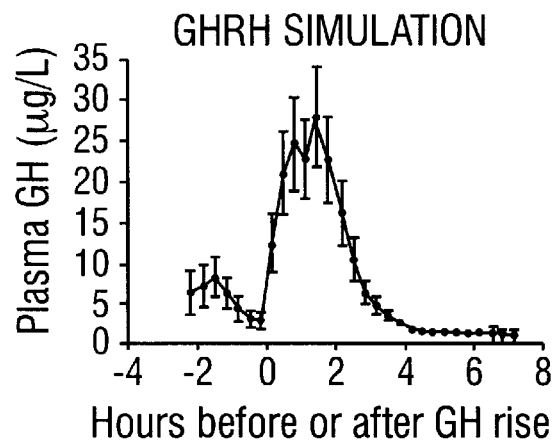
Figures 1, 5B:
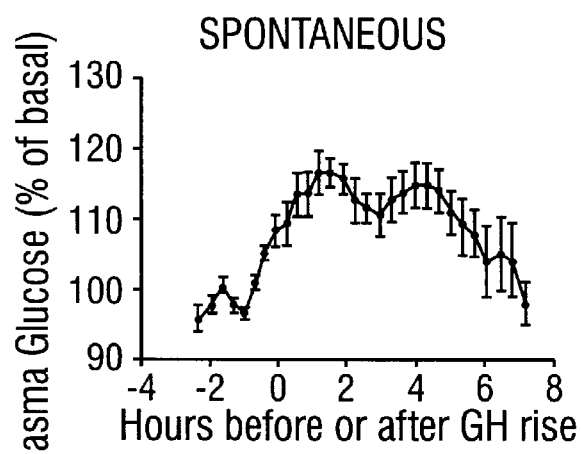
Figures 2, 5B:
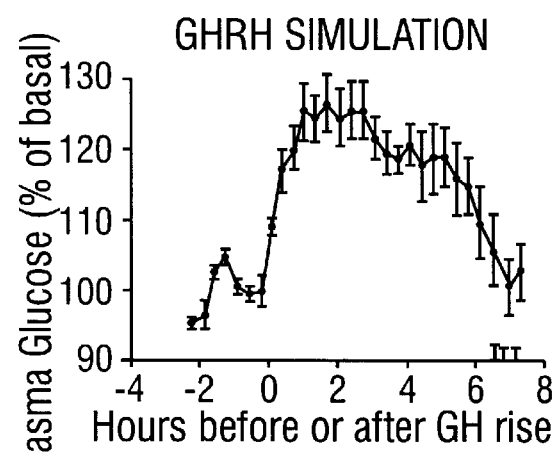
Figures 1, 5C:
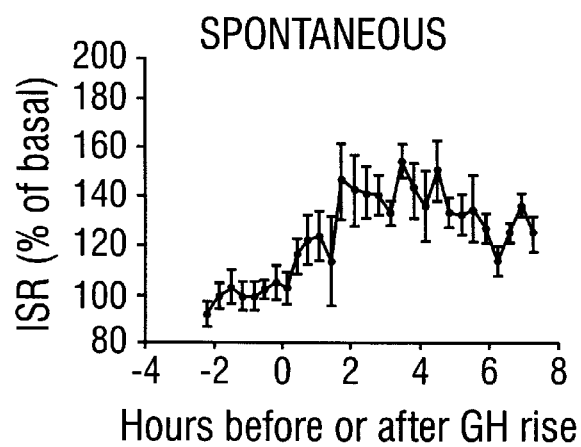
Figures 2, 5C:
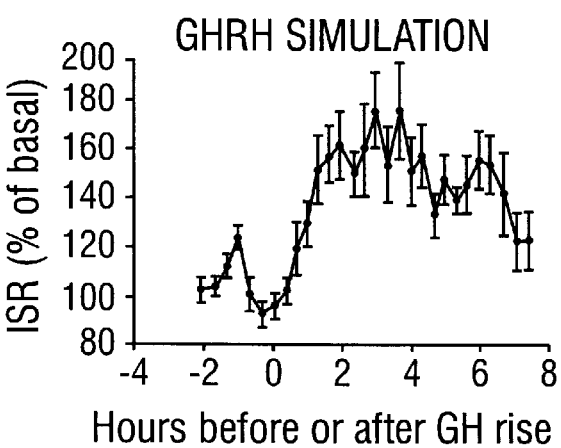
Figures 1, 6A:
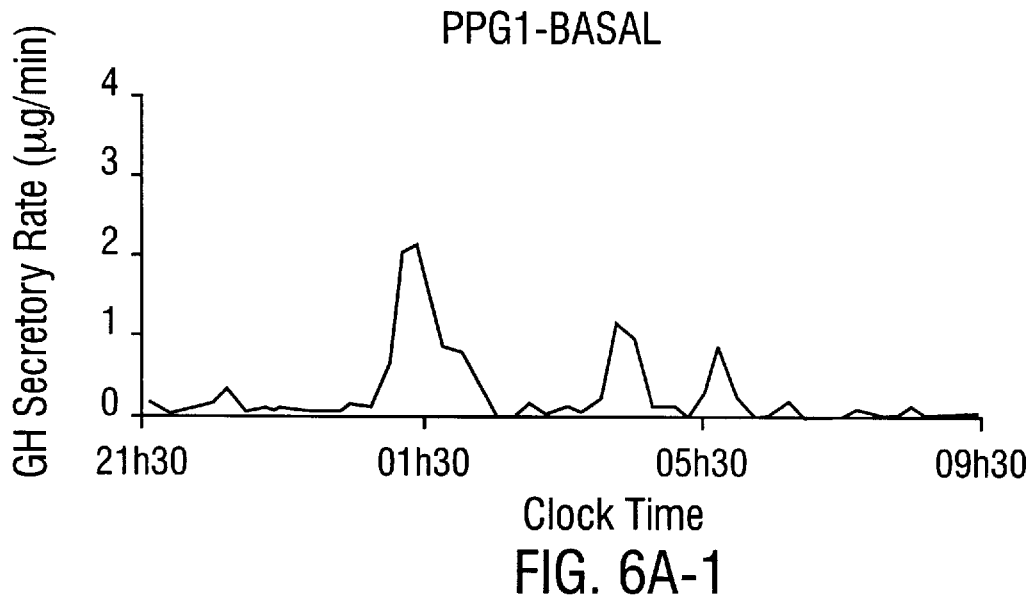
Figures 2, 6A:
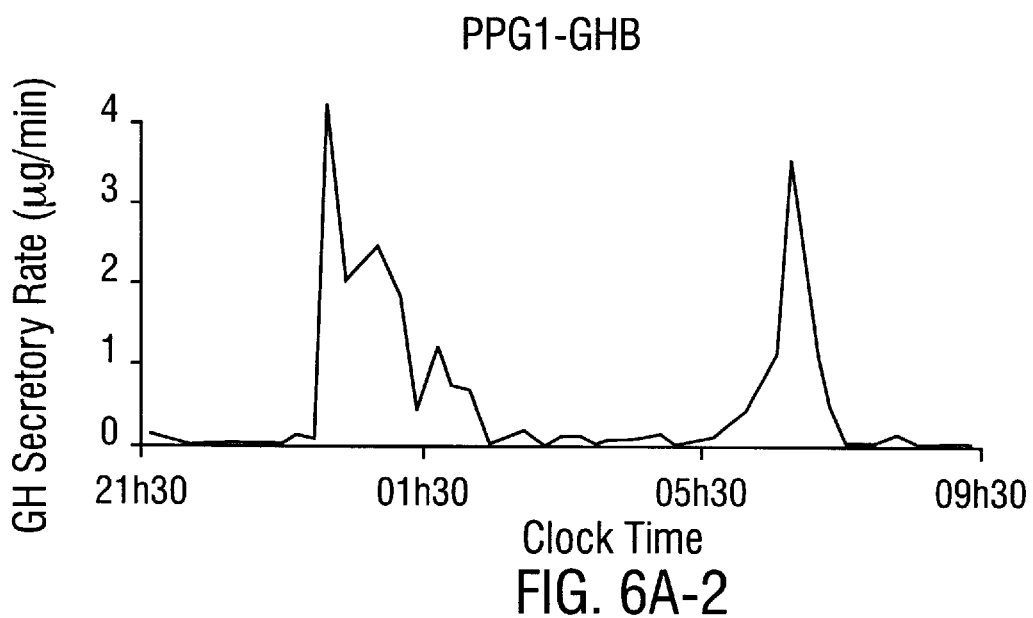
Figures 1, 6B:
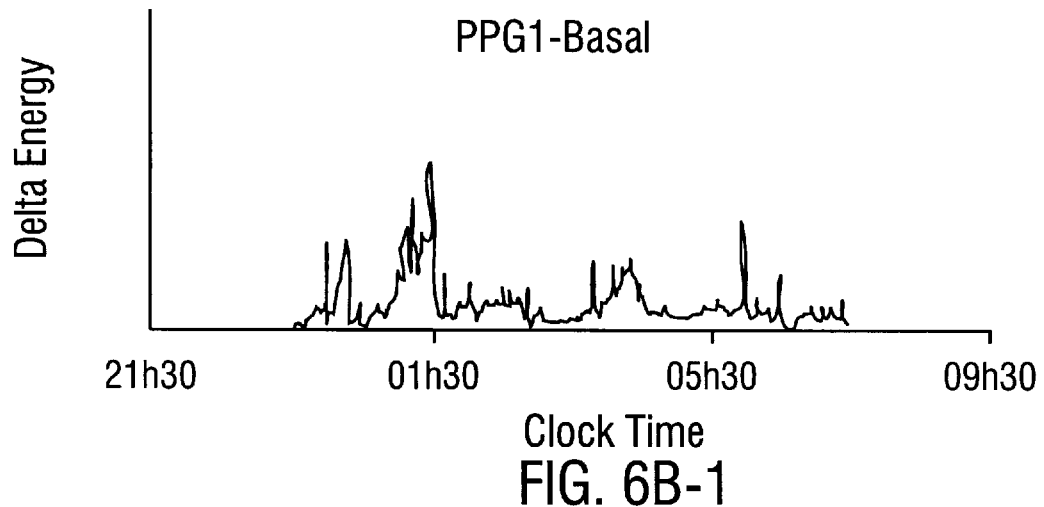
Figures 2, 6B:
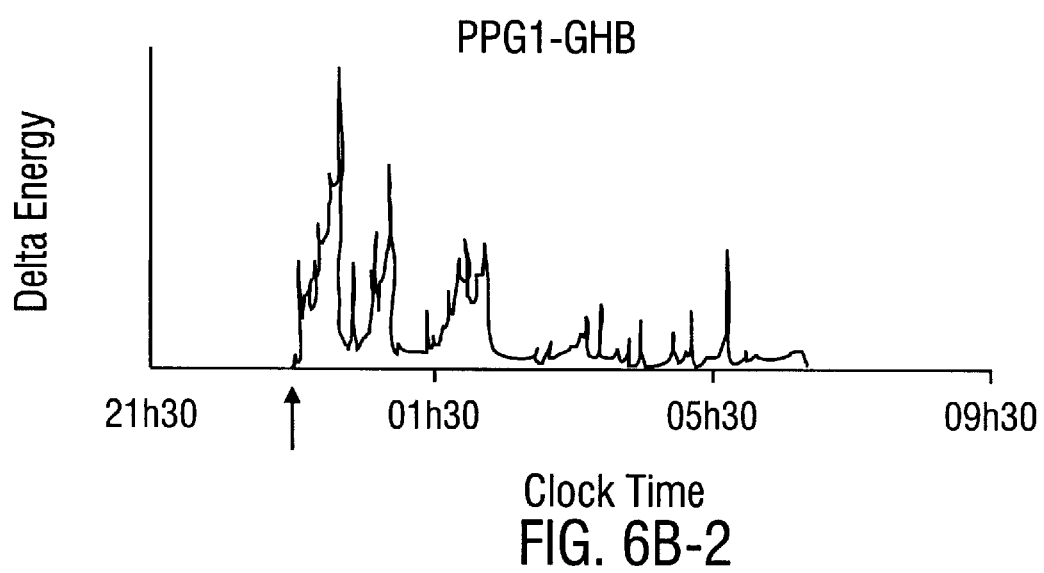
Figure 7A:
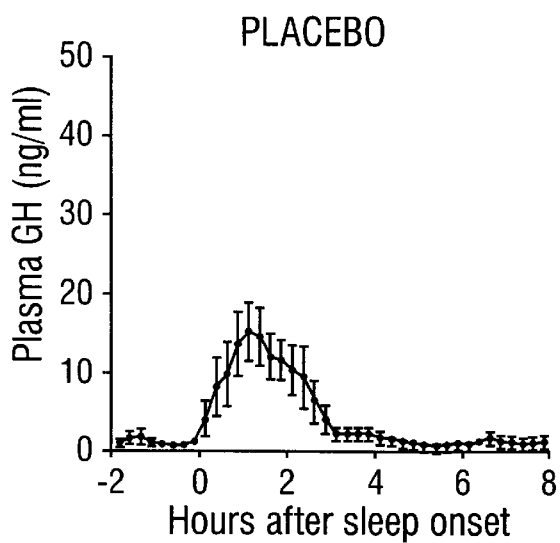
Figure 7B:
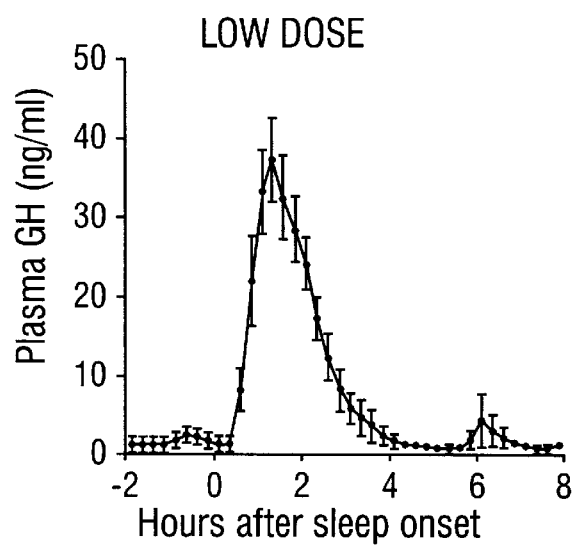
Figure 7C:
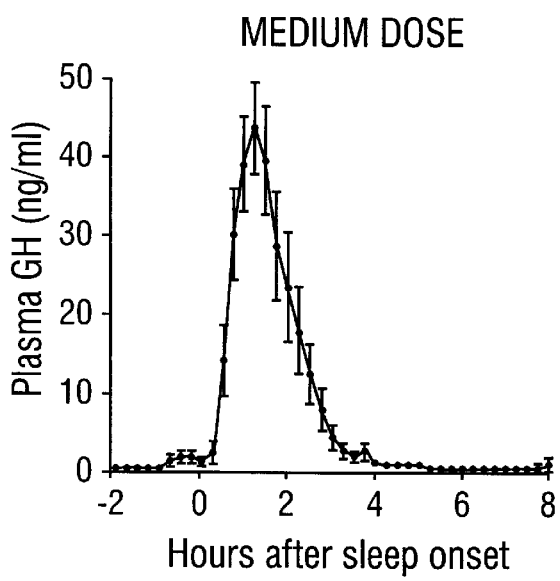
Figure 7D:
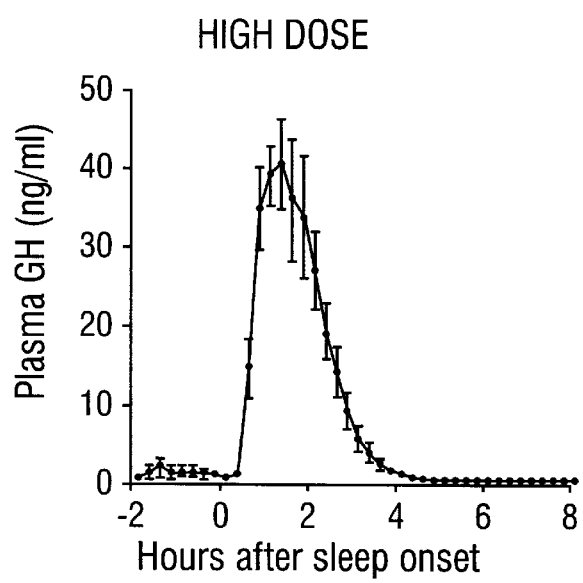
Figure 8A:
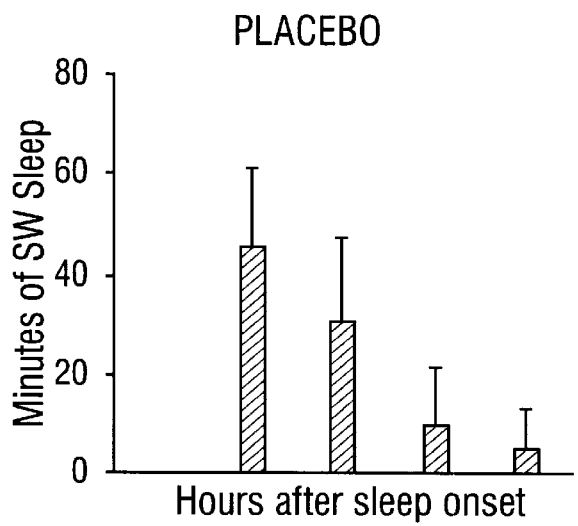
Figure 8B:
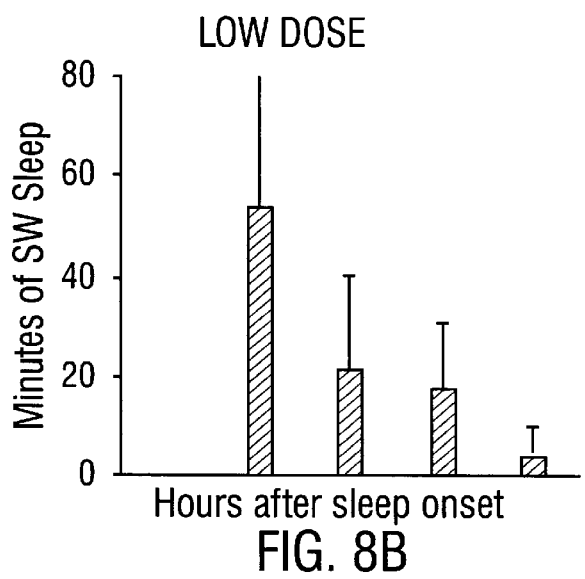
Figure 8C:
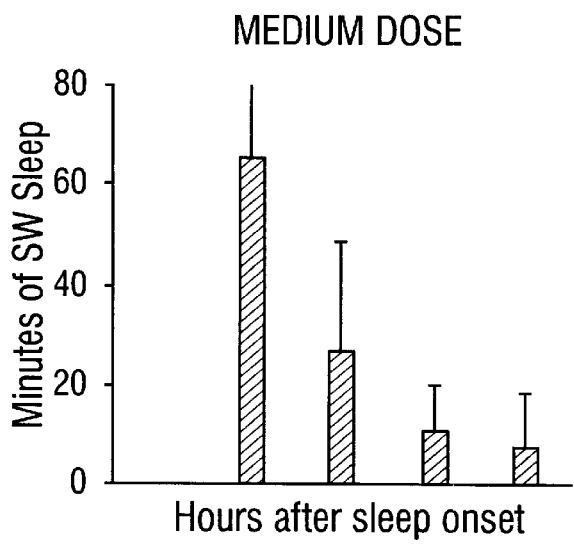
Figure 8D:
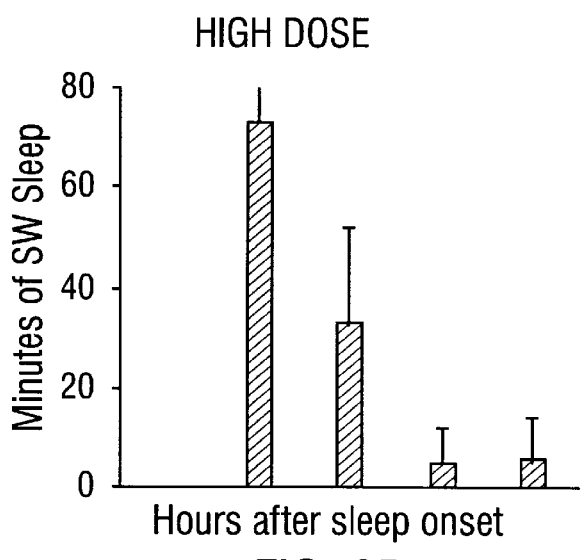
Figure 9A:
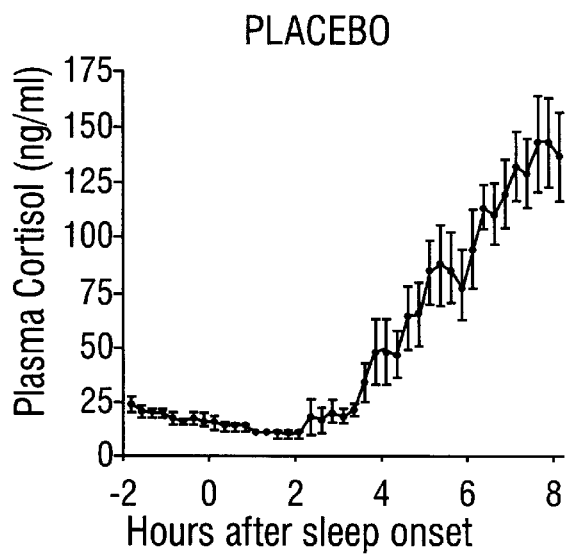
Figure 9B:
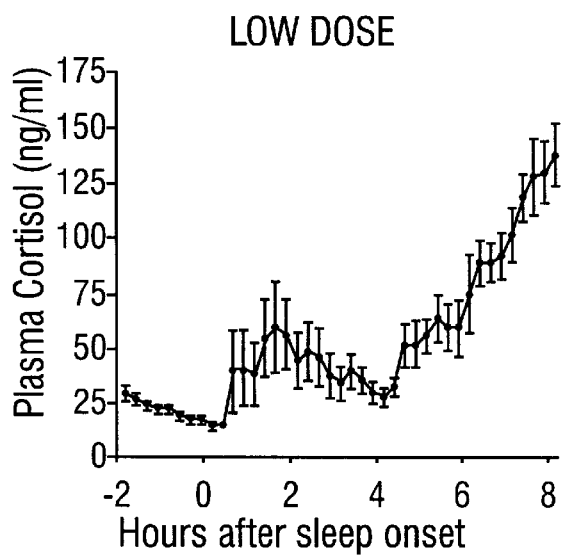
Figure 9C:
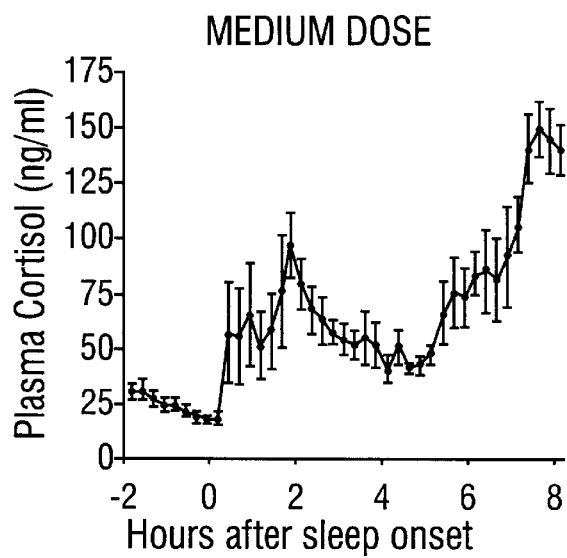
Figure 9D:
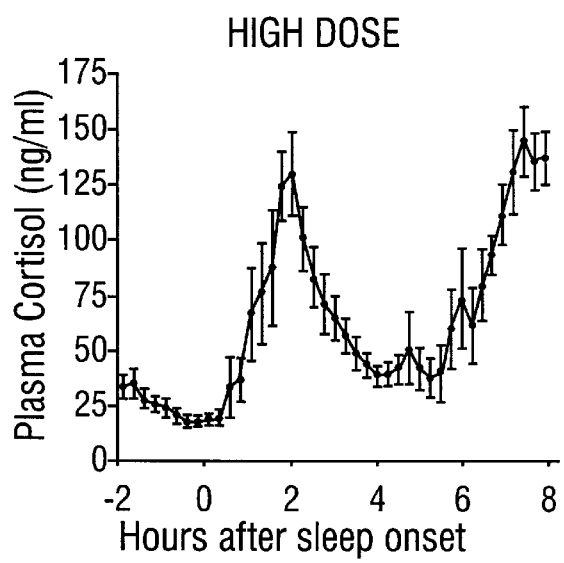
Figure 10A:
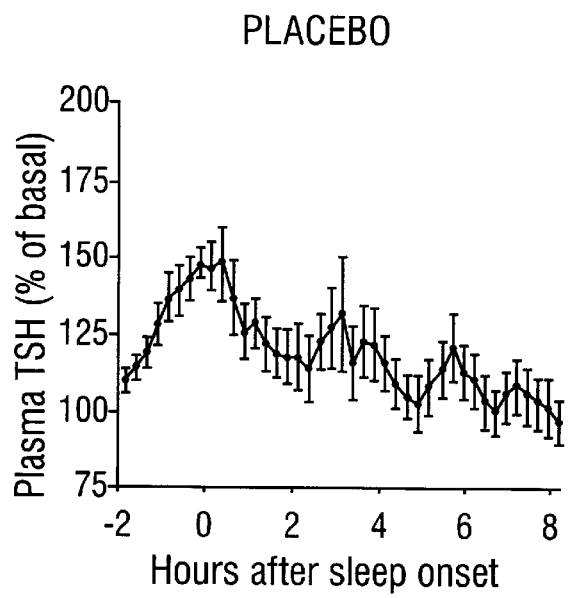
Figure 10B:
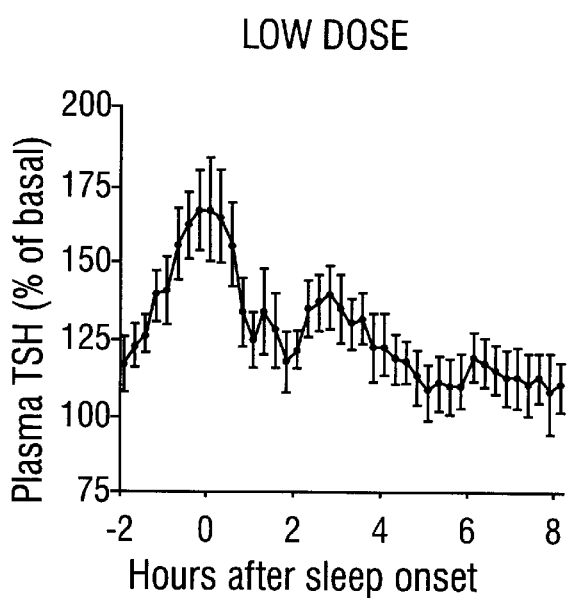
Figure 10C:
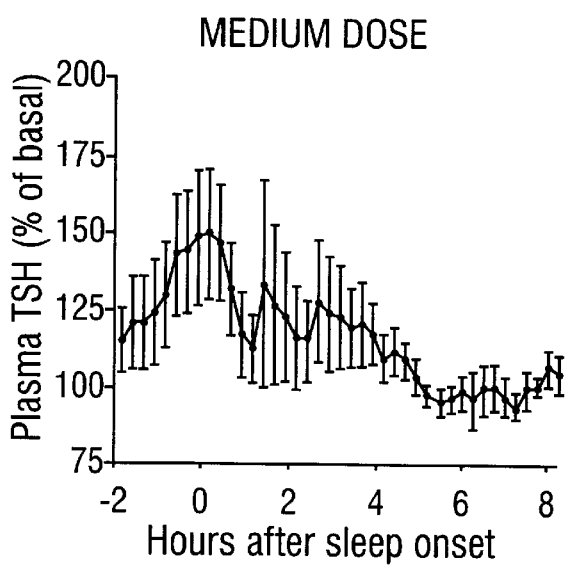
Figure 10D:
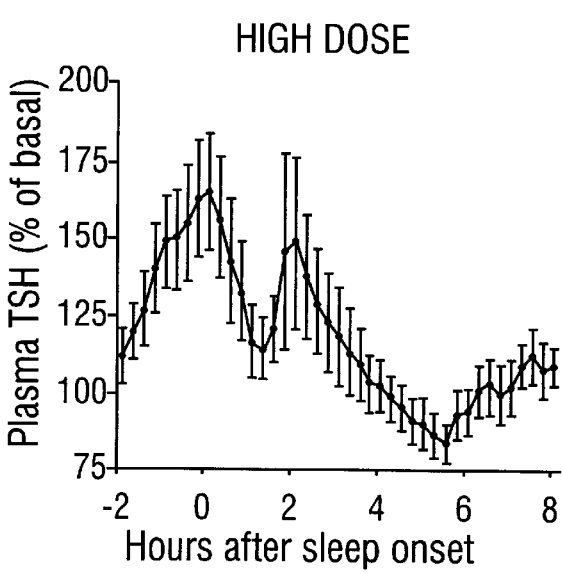
Figures 11A, 11B:
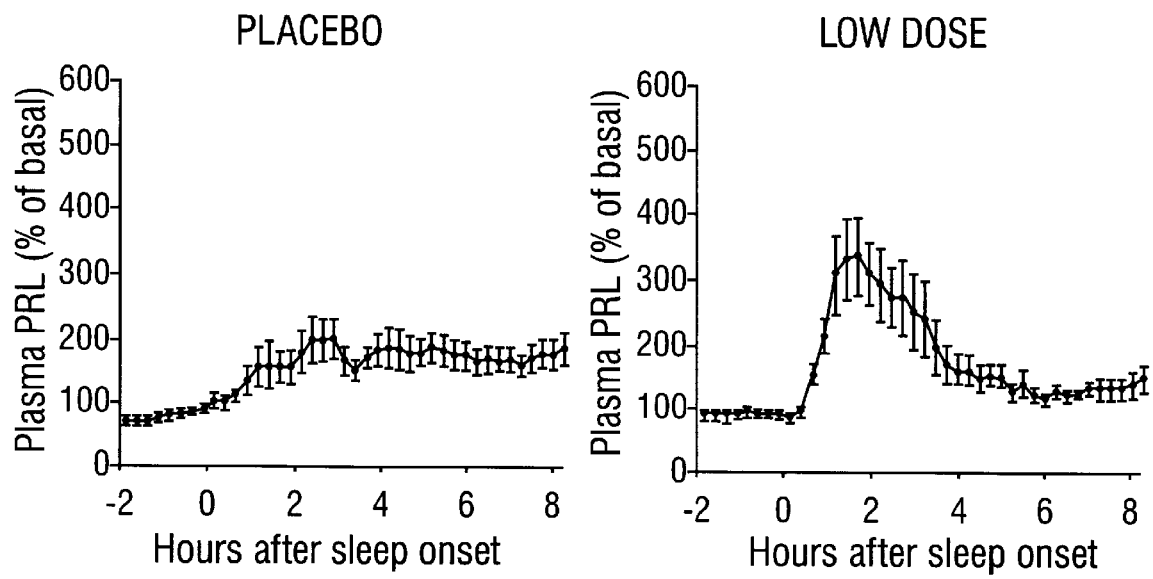
Figures 11C, 11D:
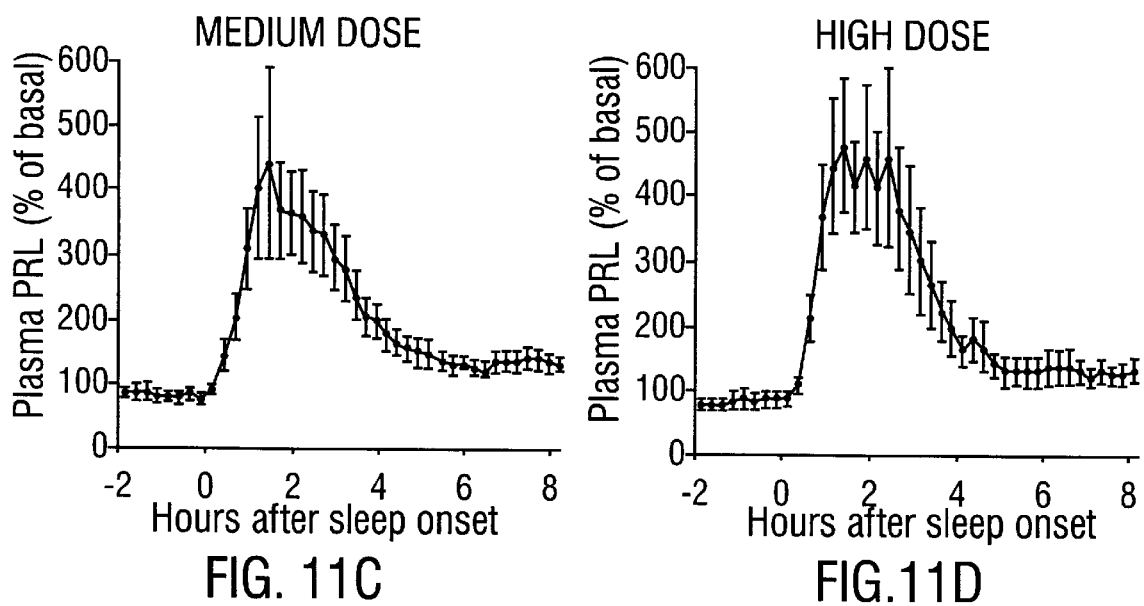

FIG. 3. Nocturnal profiles of plasma GH compared with simultaneous temporal distribution of stages Wake, I+II, SW and REM in a 72 year-old man.

FIGS. 4A-1, 4A-2 and 4A-3. Minutes of Wake (left), SW (center) and REM (right) during the first, second and third hours following GHRH injection or saline injection when the injection was given at the beginning of the first SW period.

FIGS. 4B-1, 4B-2 and 4B-3. Minutes of Wake (left), SW (center) and REM (right) during the first, second and third hours following GHRH injection or saline injection when the injection was given at the beginning of the third REM period.

FIGS. 5A-1, 5A-2, 5B-1, 5B-2, 5C-1 and 5C-2. Mean nocturnal profiles of plasma GH (top), glucose (center) and insulin secretion (bottom) in 7 young men. An injection of GHRH (right) or saline (left) was given at the beginning of the first SW period (referenced as 0 on the X-axis.

FIGS. 6A-1, 6A-2, 6B-1 and 6B-2. Temporal profiles of GH secretory rates (top) and EEF energy in the delta band (bottom) in a 45 year-old man studied under basal conditions and after oral ingestion of 3 g GHB (timing indicated by arrow).

FIGS. 7A, 7B, 7C, and 7D. Mean profiles of slow-wave sleep obtained in 7 young subjects who participated in each of four studies with bedtime administration of a placebo, low dose GHB (2.5 g), medium dose GHB (3 g) and high dose GHB (3.5 g).

FIGS. 8A, 8B, 8C and 8D. Mean profiles of plasma GH obtained in 7 young subjects who participated in each of four studies with bedtime administration of a placebo, low dose GHB (2.5 g), medium dose GHB (3 g) and high dose GHB (3.5 g).

FIGS. 9A, 9B, 9C and 9D. Mean profiles of plasma cortisol obtained in 7 young subjects who participated in each of four studies with bedtime administration of a placebo, low dose GHB (2.5 g), medium dose GHB (3 g) and high dose GHB (3.5 g).

FIGS. 10A, 10B, 10C and 10D. Mean profiles of plasma thyroid stimulating hormone obtained in 7 young subjects who participated in each of four studies with bedtime administration of a placebo, low dose GHB (2.5 g), medium dose GHB (3 g) and high dose GHB (3.5 g).

FIGS. 11A, 11B, 11C and 11D. Mean profiles of plasma prolactin obtained in 7 young subjects who participated in each of four studies with bedtime administration of a placebo, low dose GHB (2.5 g), medium dose GHB (3 g) and high dose GHB (3.5 g).

V. DETAILED DESCRIPTION OF THE INVENTION

A. Growth Hormone, γ-hydroxybutyrate and Sleep

Early human studies showed the existence of a consistent temporal association between GH secretion and the first SWS period (Sassin, Parker et al. 1969). It later was demonstrated that pulses of GH secretion which occur in late sleep also are preferentially associated with SWS stages (Golstein, Van Cauter et al. 1983). From pulse-by-pulse analysis of nocturnal profiles of GH secretory rate, it recently has been shown that approximately 70% of GH pulses during sleep are associated with the amount of SWS occurring during the phase (Van Cauter, Kerkhofs et al. 1991). Other studies have reported negative findings, however, suggesting that the relationship between SWS and GH hormone release may be coincidental (Born, Muth et al. 1988; Jarret, Greenhouse et al. 1990; McCracken, Poland et al. 1991; Steiger, Herth et al. 1987). Nonetheless, it has been suggested that a relationship may exist between sleep and GH release and, therefore, that common regulatory mechanisms exist (Obál, Payne et al. 1991a; Obál, Payne et al. 1991b). It is hypothesized that the stimulatory effects of SWS on GH secretion are mediated by GHRH release.

A number of rodent studies have indicated that the hypothalamic factor growth-hormone releasing hormone (GHRH), which controls the release of GH from the pituitary, may be involved in the modulation of sleep. Indeed, intracerebroventricular injections of GHRH in rats and rabbits increase both REM and non-REM sleep (Obál, Alfóbdi et al. 1988; Ehlers, Reed et al. 1986). Inhibition of endogenous GHRH, either by administration of competitive antagonist or by immunoneutralization, inhibits sleep (Obál, Payne et al. 1991a; Obal, Payne et al. 1991b).

In addition to the foregoing, there also are a number of other findings that indicate that GHRH secretion may be involved in the maintenance and quality of human sleep. While intravenous administration of synthetic GHRH during the daytime does not modify sleep in normal young men (Garry, Roussel et al. 1985), it has been demonstrated that GHRH administration during sleep may decrease the amount of wake time and increase SWS (Kerkhofs, Van Cauter et al. 1992). In addition, four consecutive GHRH injections at 10 pm, 11 pm, 12 am and 1 am to normal, young males also showed improved sleep (Steiger, Guldner et al. 1991).

Age-related decreases in GH secretion have been well documented in both men and women (Finkelstein, Roffwarg et al. 1972; Ho, Evans et al. 1987; Iranmanesh, Lizarralde et al. 1991; Prinz, Weitzman et al. 1983, van Coevorden, Mockel et al. 1991; Vermeulen 1987) . The mechanisms underlying reduced GH secretion in the aged have not been completely elucidated. A decreased responsiveness of the somatotroph to stimulation by exogenous GHRH has clearly been demonstrated in older adults of both sexes (Lang, Schernthaner et al. 1987; Shibasaki, Shizume et al. 1984). Though still controversial, adults treated with synthetic GH report an overall improvement in the quality of life, including higher energy levels and better mood (Degerblad, Almkvist et al. 1990; McCauley 1989).

Oyama and Takiguchi (1970) measured the effects of γ-hydroxybutyrate anesthesia on GH release in ten patients undergoing elective surgery. While increases in plasma GH levels were observed over a 45 min period (followed by a drop to normal during recovery), the simultaneous administration of $N_2O$ and pretreatment with pentobarbital, atropine and meperidine made it unclear whether the results were the result of one or more of the drugs.

Takahara et al. (1977) described a study in which γ-hydroxybutyrate was injected into subjects and the effects of GH release observed at 15, 30, 45, 60, 90 and 120 minutes following treatment. Plasma GH levels increased significantly at 30 min and peaked after 60 min, followed by a gradual decrease. Prolactin levels also rose after treatment. The study was performed during the daytime and reported that 5 out of 6 subjects fell asleep following GHB injection. Sleep was not polygraphically recorded, however, and thus it is unclear whether the enhancement of GH secretion was directly related to GHB or indirectly due to increases in SWS.

Scharf et al. (1985) reported the oral administration of γ-hydroxybutyrate to subjects with polysomnographically confirmed narcolepsy. The drug was given prior to and during a nocturnal, eight-hour sleep period at a total of 5 to 7 grams. Sleep efficiency (sleep time/total time) increased as did the percentage of stage 2 and 3 sleep. There was no discussion of the effects on GH release nor was there any discussion of age-related disorders in GH secretion.

Recently, γ-hydroxybutyrate has found illicit use with some body builders and others seeking to reduce body fat. Excessive use has, in rare cases, led to side effects such as headaches, nausea, dizziness, myoclonic jerking, abrupt drowsiness and even short-term coma. In at least one instance, γ-hydroxybutyrate was marketed as a "nighttime GH releaser designed to provide a maximum GH release during the first two hours of sleep, as well as a pronounced soporific (sleep-inducing) effect." While these illicit uses of GHB have established its hypnotic properties, there are few good scientific studies demonstrating its sleep-enhancing properties in normal subjects.

However, there appear to be no valid reports stemming from these recent, illicit uses of γ-hydroxybutyrate that confirm improved sleep patterns. One article indicated that two doses of 2 to 3 grams each, administered four hours apart, produced a variety of central nervous system effects including abrupt onset sleep, sleep paralysis, sleep walking, hallucinations, enuresis and myoclonic movements (Mamelak et al. 1986). However, these effects are typical in narcoleptic patients. Administration of γ-hydroxybutyrate to non-narcoleptic patients can induce narcoleptic like side effects, but only with the initial dose; these effects may be dose dependent. Enuresis and sleep walking are more common and likely to be related to the induction of SWS. Another authority reported that intravenous or oral administration of 40 to 50 mg/kg of γ-hydroxybutyrate results in a somnolent state which is followed, in about 5 to 15 minutes, by an arousable sleep. Higher doses of 60 to 70 mg/kg results in an unarousable coma lasting between one and two hours (Vickers 1967).

B. The Present Invention

Typically, the age-associated decrease in GH levels has been viewed merely as a hormonal alteration resulting from decreased GH output from the pituitary. The present invention approaches this problem from a different point of view, namely, that the loss of SWS with aging has eliminated the signal which normally stimulates GH release from the pituitary, thereby lowering GH levels. Put another way, if increased SWS patterns can be established, the GH secretion associated with this sleep state may result in significantly elevated GH levels and, moreover, do so in a physiologic manner (i.e., without overdose toxicity).

While many studies have shown that there is a temporal association between the first GH pulse occurring after sleep onset and the first episode of SWS, as estimated by stages III and IV, the concept that SWS is a consistent stimulus of GH secretion has remained controversial. Studies now have been conducted that more clearly establish the relationship between GH and sleep and the GH-related sleep deficiencies in the elderly. Furthermore, it also has been discovered that oral administration of the compound γ-hydroxybutyrate can increase SWS in subjects whose SWS has been impaired by age-related diminution of GH secretion.

C. Definitions

Catabolic state: A state involving the conversion of fat or protein into readily usable energy.

Elderly: Elderly is used in the context of the present invention as any individual exhibiting age-related diminution in GH release. These effects usually are evident by about age 40, but may occur earlier in some individuals. It also may be useful to break down treatment of individuals based on age, for example, those persons aged 40, 45, 50, 55 and 60 and above. Because of the correlation with SWS and GH release, another way of classifying individuals is by their SWS time. Average SWS for the young is about 87±61 min per night while for the elderly, the figure is about 26±30. Thus, adults with less that about 50 min per night SWS would qualify has having age-related diminution in GH release.

γ-hydroxybutyrate: $C_4H_8O_3$ (Mw 104.2), having the formula

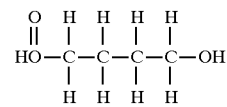

Initially synthesized in 1960 as a γ-aminobutyrate analog that was capable of crossing the blood-brain barrier, γ-hydroxybutyrate was anticipated to be a developed as an anesthetic. Lack of analgesia and occurrence of petit and grand mal seizures diminished enthusiasm for this application, however. In 1963, it was found to be a naturally-occurring substance in the human brain and now is hypothesized to be a neurotransmitter like the related compounds γ-aminobutyrate and glutamic acid. The site and mechanism of action for this drug, resulting in such clinical effects as increased SWS, reduction of narcolepsy and the aforementioned side effects, remain unknown.

γ-hydroxybutyrate-related molecules: This term includes compounds that are capable of increasing the release of GH and/or prolactin through the same mechanism as does γ-hydroxybutyrate.

Growth Hormone (GH) Growth hormone, also known as somatotropin, is a peptide hormone containing 191 amino acids and having a molecular weight of about 22 kD. It is secreted from the pituitary gland, stimulates the growth of all tissues that are capable of growing, increases protein synthesis, decreases glucose utilization, causes an increase in weight and length of the body, alters protein, carbohydrate, fat, bone and steroid metabolism and modulates immune function.

Growth Hormone Releasing Hormone (GHRH): Secreted from the hypothalamus, growth hormone releasing hormone (or factor) acts to increase the secretion of growth hormone by the pituitary gland. There is evidence that GHRH contributes to the regulation of sleep.

Prolactin: Also known as luteotropin or LTH, prolactin is a polypeptide hormone of 23 kD that is produced by the adenohypophysial gland. Its synergistic effect with estrogen promotes mammary gland proliferation and also brings about the release of progesterone from lutein cells, rendering the uterine mucosa receptive to embedding of the ovum, should fertilization occur. In the non-lactating female, the functions of prolactin are less well understood, although immunity-promoting properties have been demonstrated.

D. Active Ingredients

"Active Ingredients" according to the present invention include γ-hydroxybutyrate and related molecules. Another name for this compound is 4-hydroxybutyric acid. The sodium salt is the typical form in which the compound is stored. These compounds are available from various commercial sources, for example, Sigma Chemicals, St. Louis, Mo. Prodrugs that are converted in vivo to γ-hydroxybutyrate also are within

E. Pharmaceutical Compositions

Pharmaceutical compositions containing the active ingredient according to the present invention may be administered as pharmaceutically acceptable compositions that include physiologically acceptable carriers, buffers or other excipients. For example, pharmaceutical compositions may be administered in the form of injectable compositions either as liquid solutions or suspensions; solid forms suitable for solution or suspension in liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration are preferred. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

Typical dosages will be between 2.0 and 5.0 grams. Preferred dosages are 2.25 to 3.75 grams with 2.5, 3.0 and 3.5 grams being most preferred. On a mg/kg basis, 32–53 mg/kg is the preferred range with 40–45 mg/kg being preferred. Generally, one dose per night is administered. Delayed release formulations are another embodiment of the present invention and may have somewhat greater or less total doses depending on the formulation.

F. Therapeutic Regimens

According to the present invention, the pharmaceutical composition is administered to subjects just prior to retiring. Typically, this will be within the last hour prior to retiring but may be one-half hour or less prior to retiring. It also may be desirable to administer a second, or even a third dose during the normal sleep period. The administration may be via any common route including oral, nasal, buccal, rectal, vaginal, or topical. Alternatively, administration will be by intradermal subcutaneous, intramuscular, intraperitoneal, or intravenous injection. In a particular embodiment, the pharmaceutical composition is administered in a single oral dose formulation about one-half hour before retiring.

The term "unit dose" refers to physically discrete units suitable for use in humans, each unit containing a predetermined quantity of the pharmaceutical composition calculated to produce the desired response in association with its administration, i.e., the appropriate carrier, route and treatment regimen. The quantity to be administered, both according to number of treatments and unit dose, depends on the subject to be treated. Person having a greater or lesser reduction in growth hormone release will be given lesser or greater amounts, respectively, of the active ingredient. Precise amounts of the therapeutic composition also depend on the judgment of the practitioner and are peculiar to each individual.

Various different subjects may benefit from this type of treatment. Typically, individuals of age forty or older will exhibit some degree of reduced SWS. For the purposes of this application, individuals experiencing less than about 50 minutes of SWS per night can be considered "elderly." Such persons can be patients in catabolic states, including burn victims, recovering surgery patients and patients suffering chronic protein loss, usually as a result of chronic illness (cancer, AIDS, etc.).

VI. EXAMPLES

A. Example 1

Alterations of Hormonal and Sleep Profiles in the Elderly

The 24-hour profiles of GH, melatonin and cortisol were obtained at 15 minute intervals in eight healthy active elderly men (ages 67–84) and 8 normal young male adults (20–27). The study was preceded by 3–5 nights of habituation to the laboratory and sleep was polygraphically recorded. FIG. 1A–E show the mean profiles of cortisol, melatonin and GH in old and young subjects, together with the mean profiles of the distribution of stages III+IV (SWS) and stage REM. The total amount of GH secreted over the 24-hour cycle was reduced by approximately three-fold in the elderly men compared with the younger subjects. In 3 of the 8 elderly subjects, the sleep-onset GH pulse was not present. The total duration of stages III and IV averaged 26±30 min in the elderly, as compared to 87±61 min in the young subjects ($p<0.02$). REM stages were shifted towards the beginning of the sleep period in the elderly. Indeed, the time necessary to accumulate 50% of the total amount of REM was 253±83 min in the elderly as compared to 328+48 in the young men. This advance of REM stage distribution was paralleled with an advance of the cortisol rhythm such that the circadian rise towards the morning maximum occurred, on average, 63 min earlier in the elderly than in the young men ($p<0.02$). This earlier timing of the cortisol rhythm was accompanied by a reduction in amplitude (old: 67±13% of the mean; young: 88±17% of the mean; $p<0.01$). Daytime levels of melatonin were similar in young and old subjects, but the level of the nocturnal maximum was reduced by half in the elderly volunteers (average in 159±112 pmol/L versus 304±124 pmol/L in young subjects; $p<0.01$). There also was an advance of the rhythm in the elderly subjects, since the melatonin levels reached 50% of their nocturnal maximum approximately one and a half hours earlier than in the young men.

These data demonstrate that senescence is associated with a 50% reduction in nocturnal melatonin output and an even larger reduction in sleep-related GH secretion and SWS.

Dampening and advance of circadian rhythmicity were indicated by a reduced amplitude and advanced timing of both the cortisol and the melatonin rhythms as well as by a reduction and advance in REM stages.

B. Example 2

Relationship Between SWS and GH Release

Eight normal men, ages 24–31, participated in four separate 16-hour studies involving either normal sleep times (23:00–7:00) or delayed sleep times (4:00–12:00). GH levels were measured at 15 min intervals throughout the study and GH secretory rates were calculated by deconvolution using a one-compartment model for GH distribution and metabolism. A total of 83 GH secretory pulses were observed during sleep in these studies. The correlation between amount of GH secreted and minutes of SW sleep is depicted in FIG. 2. The correlation remained significant when sleep-onset pulses were excluded and only pulses occurring in later sleep considered (R=0.57, p<0.01).

In the elderly, however, this correlation between occurrences of stages III and IV and GH secretion is not consistently observed, even for sleep-onset pulses. FIG. 3 shows an example where a significant GH pulse occurred after sleep onset in the absence of significant amounts of stages III +IV. Power spectral analysis of the delta waves may resolve this apparent contradiction by permitting an estimation of delta power and delta count.

Previously, it has been demonstrated that awakenings interrupting nocturnal sleep modulate spontaneous as well as stimulated GH secretion (Van Cauter, Caufriez et al. 1992; Van Cauter, Kerkhofs et al. 1992). Specifically, awakenings which occur during ongoing GH secretion inhibit the secretory process, even when secretion has occurred in response to stimulation by exogenous GHRH administration. Thus, the relationship between sleep and GH secretion is intricate, as GH release in early sleep may contribute to sleep maintenance in the later part of the night, whereas awakenings in the later part of the night will inhibit GH release. In older adults, nocturnal awakenings are more frequent, even in early sleep, and could therefore contribute to the overall decrease in GH secretion during sleep.

C. Example 3

Effects of GHRH Injections on Sleep

Animal studies have indicated that injection of the hypothalamic factor growth hormone releasing hormone (GHRH) results in hypnotic effects. In man, however, administration of GHRH at bedtime in normal young adults does not modify sleep duration and architecture. To further evaluate the possible effects of GHRH on sleep, the inventors have administered an intravenous injection of 0.3 $\mu$g/kg to seven normal young men on two separate occasions: (i) after one minute of SWS during the first episode of SWS; (ii) after one minute of REM sleep during the third episode of REM sleep. The volunteers participated in two additional studies with saline infusions which served as controls. The amounts of wake, stages II +IV (SWS) and REM were calculated for each hour following the injection. The results are shown in FIGS. 4A-1, 4A-2, 4A-3 4B-1, 4B-2 and 4B-3. Confirming a previous report (Garry, Roussel et al., 1985), the inventors failed to detect significant effects of GHRH on sleep when administered at bedtime. When GHRH was administered at the beginning of the third REM period, i.e., later in the night, the amount of wake was significantly reduced and the amount of SWS was significantly increased. These results indicate that GHRH stimulates SWS and reduces nocturnal awakenings when administered at a time when sleep is shallow and awakenings are more frequent and, further, may decrease nocturnal wakefulness and enhance delta sleep in the later part of the night.

D. Example 4

Effects of γHydroxyburyrate on Insulin Secretion and Glucose Levels

To examine whether sleep-related elevations in glucose and insulin secretion could be at least partially mediated by GH, plasma GH levels were measured on samples obtained from young men and correlations between GH secretion during sleep and sleep-associated rises in glucose and insulin secretion were calculated. A significant correlation between the amount of GH secreted and the increase in glucose, but not insulin secretion, was found (r=0.73, p<0.002). To further investigate the role of GH in mediating sleep-associated decreases in glucose tolerance, the inventors amplified nocturnal GH secretion by an appropriately timed injection of GHRH. Eight normal non-obese men (ages 22–30 y) were studied on each of two separate occasions during glucose infusion at a constant rate of 5 g/kg/24 h over a 37 h period. The subjects slept from 2300 to 0700 and sleep was polygraphically monitored. Oral feeding was withheld. In the first study (baseline), the subjects received saline through the sampling catheter. In the second study, an injection of 25 $\mu$g of GHRH was administered after 1 min of slow-wave sleep as established by extemporaneous examination of the recordings. FIGS. 5A-1, 5A-2, 5B-1, 5B-2, 5C-1 and 5C-2 illustrate the results. Injection of GHRH resulted in a marked amplification of the sleep onset GH pulse, with peak levels averaging 13.2±10.3 $\mu$g/L under baseline conditions and 34.3±15.4 $\mu$g/L after GHRH injection (upper panels of FIG. 5). The sleep-associated rise of glucose also was significantly increased, as the mean area under the curve increased by more than two-fold following GHRH injection (middle panels of FIGS. 5A-1, 5A-2, 5B-1, 5B-2, 5C-1 and 5C-2; p<0.02). While a trend for a similar increase in insulin secretion was apparent (lower panels of FIGS. 5A-1, 5A-2, 5B-1, 5B-2, 5C-1 and 5C-2), the difference between saline and GHRH conditions failed to reach significance.

E. Example 5

Effects of γ-Hydroxybutyrate on Sleep and GH Secretion

The SWS-inductive properties of y-hydroxybutyrate were examined in studies on two healthy subjects -a forty-five year-old man and a forty-four year-old woman. Following one night of habituation to the laboratory and sleep recording procedures, the subjects were admitted on two consecutive nights around 20:00 and a catheter for venous sampling was inserted in a forearm vein. Blood sampling at 15 min intervals started at 21:00 and continued 12 hours. The subjects were recumbent in a dark room from 23:30 until spontaneous morning awakening. Sleep was polygraphically recorded and spectral analysis was performed. Computer-generated sleep stages were visually checked against the polygraphic records by an experienced EEG technician and corrected where appropriate. One of the nights, the subjects ingested 3 grams of γ-hydroxybutyrate in an orange-flavored drink and the other night served as the baseline. The order of the γ-hydroxybutyrate and baseline studies was randomized.

In both subjects, the amount of SWS in the first part of the night was three-fold higher after γ-hydroxybutyrate treatment when compared to the baseline conditions. The sleep-onset pulse of GH in the male volunteer was increased from 102 μg to 251 μg with γ-hydroxybutyrate treatment. In the female volunteer, the amount of GH secreted in the sleep-onset pulse was 158 μg under baseline conditions and 223 μg after γ-hydroxybutyrate treatment. Analysis of the temporal coincidence between increases in GH secretory (derived from plasma GH levels by deconvolution using a one-compartment model with a half-life of 19 min) and absolute energy in the delta band (0.5–3 Hz) in each 20 sec epoch of recording indicates that each increase in energy in the delta band was followed by a rise in GH secretory rate. These data are show in FIGS. 6A-1, 6A-2, 6B-1 and 6B-2.

F. Example 6

In a study similar to that described in Example 3, seven young subjects participated in each of four studies with bedtime administration of placebo, low, medium and high doses of γ-hydroxybutyrate. There was a significant stimulation of SWS, particularly in the first two hours of sleep. GH and prolactin release also increased with increasing dosage. These data are illustrated in FIGS. 7A, 7B, 7C, 7D, 8A, 8B, 8C, 8D, 9A, 9B, 9C, 9D, 10A, 10B, 10C, 10D, 11A, 11B, 11C and 11D.

VII. REFERENCES

The following references, to the extent that they provide exemplary procedural or other details supplementary to those set forth herein, are specifically incorporated herein by reference:

U.S. Pat. No. 5,206,235

Born, Muth et al., Psychoneuroendocrinology 13: 233–243, 1988

Degerblad, Almkvist et al., Acta Endocrinol 123: 185–193, 1990

Ehlers, Reed et al., Neuroendocrinology 42: 467–474, 1986

Finkelstein, Roffwarg et al., J. Clin. Endocrinol Metab. 35: 665–670, 1972

Garry, Roussel et al., Acta Endocrinol 110: 158–163, 1985

Golstein, Van Cauter et al., J. Clin. Endocrinol Metab. 56: 433–440, 1983

Ho, Evans et al., J. Clin. Endocrinol Metab. 64: 51–58, 1987

Iranmanesh, Lizarralde et al., J. Clin. Endocrinol. Metab. 73: 1081–1088, 1991

Iranmanesh, Lizarralde et al., J. Clin. Endocrinol. Metab. 72: 108–115, 1991

Jarret, Greenhouse et al., Biol. Psychiatry 27: 497–509, 1990

Kerkhofs, Van Cauter et al., Am. J. Physiol. 264:E592–E598, 1993

Lang, Schernthaner et al., J. Clin. Endocrinol. Metab. 65: 535–540, 1987

Mamelak et al., Sleep 9: 285–289, 1986

McCauley, G. A., Acta Paediatr Scand (suppl) 356: 70–72, 1989

McCracken, Poland et al., J. Clin. Endocrinol Metab. 72: 90–95, 1991

Obál, Alfödi et al., Am. J. Physiol. 255: R310–R316, 1988

Obál, Payne et al., Sleep Res. 20A: 192, 1991a

Obál, Payne et al., Brain Res. 557: 149–153 1991b

Oyama and Takiguchi, Travail recu lo, 6: 289–297, Japan (1970)

Prinz, Weitzman et al., J. Gerontol. 38: 519–524, 1983

Sassin, Parker et al., Science. 165: 513–515, 1969

Scharf et al., The Journal of Clinical Psychiatry 46: 222–225, 1985

Shibasaki, Shizume et al., J. Clin. Endocrinol. Metab. 58: 212–214, 1984

Steiger, Herth et al., Acta Endocrinol (Copenh.), 116: 36–42, 1987

Steiger, Guldner et al., Sleep Res. 20A: 195, 1991

Takahara et al., J. Clin. Endocrinol Metab. 44: 1014–1017 (1977)

Van Cauter, Kerkhofs et al., Arch. Gen. Psychiatry 48: 348–356, 1991

Van Cauter, Kerkhofs et al., J. Clin. Endocrinol Metab. 74: 1441–1450, 1992

Van Cauter, Caufriez et al., J. Clin. Endocrinol Metab. 74: 1451–1459, 1992 van Coevorden, Mockel et al., American Physiological Society, 91: 0193–1849, E651–E661, 1991

Vermeulen, A., J. Clin. Endocrinol. Metab. 64: 884–888, 1987

Vickers, International Anesthesiology Clinics 7: 75–89, 1967

What is claimed is:

1. A method for stimulating the release of growth hormone or prolactin in a human subject comprising the steps of:

(a) identifying a human subject having age-related suppression of growth hormone or prolactin release; and then (b) orally administering to said human subject, within one hour prior to retiring, a unit dose of γ-hydroxybutyrate of about 2 to 5 g, said unit dose effective to increase the release of growth hormone or prolactin.

2. The method of claim 1, wherein said subject is at least forty years old.

3. The method of claim 2, wherein said subject is at least fifty years old.

4. The method of claim 3, wherein said subject is at least sixty years old.

5. The method of claim 2, wherein said subject is experiencing difficulty sleeping.

6. The method of claim 1, wherein said administration occurs one-half hour prior to retiring.

7. The method of claim 1, wherein said γ-hydroxybutyrate is administered in a controlled release formulation.

8. The method of claim 1, further comprising coadministering at least one growth hormone secretagogue.

9. The method of claim 8, wherein said growth hormone secretagogue is growth hormone releasing peptide.

10. The method of claim 1, wherein the effective amount of γ-hydroxybutyrate is 2.5 grams.

11. The method of claim 1, wherein the effective amount of γ-hydroxybutyrate is 3.0 grams.

12. The method of claim 1, wherein the effective amount of γ-hydroxybutyrate is 3.5 grams.

13. A method for stimulating the release of growth hormone or prolactin in a human subject comprising the steps of:

(a) identifying a human subject experiencing severe trauma or chronic illness; and then (b) orally administering to said human subject a unit dose of γ-hydroxybutyrate of about 2 to 5 g, said unit dose effective to increase the release of growth hormone or prolactin.

14. The method of claim 13, wherein said subject is experiencing severe trauma.

15. The method of claim 14, wherein said severe trauma is burns.

16. The method of claim 14, wherein said severe trauma is surgery.

17. The method of claim 13, wherein said subject is experiencing chronic illness.

18. The method of claim 8, wherein said growth hormone secretagogue is a functional analog of growth hormone releasing peptide.

19. The method of claim 13, wherein the effective amount of γ-hydroxybutyrate is 2.5 grams.

20. The method of claim 13, wherein the effective amount of γ-hydroxybutyrate is 3.0 grams.

21. The method of claim 13, wherein the effective amount of γ-hydroxybutyrate is 3.5 grams.

* * * * *

UNITED STATES PATENT AND TRADEMARK OFFICE
CERTIFICATE OF CORRECTION

PATENT NO.    :   5,840,331

DATED         :   November 24, 1998

INVENTOR(S)   :   Van Cauter et al.

It is certified that error appears in the above-identified patent and that said Letters Patent is hereby corrected as shown below:

On the title page, item 54, lines 1-4, please delete "USE OF γ-HYDROXYBUTYRATE FOR THE STIMULATION OF SLEEP-RELATED SECRETION GROWTH HORMONE AND PROLACTIN" and insert therefor: -- USE OF γ-HYDROXYBUTYRATE FOR THE STIMULATION OF SLEEP-RELATED GROWTH HORMONE AND PROLACTIN SECRETION --.

Signed and Sealed this

Second Day of March, 1999

*Attest:*

Q. TODD DICKINSON

*Attesting Officer*   Acting Commissioner of Patents and Trademarks